(12) United States Patent
Roschin et al.

(10) Patent No.: US 9,730,901 B2
(45) Date of Patent: *Aug. 15, 2017

(54) AGENT, PHARMACEUTICAL COMPOSITION, AND METHOD FOR TREATING THE ETHYL ALCOHOL AND/OR NARCOTIC DEPENDENCE

(71) Applicants: Viktor Ivanovich Roschin, St. Petersburg (RU); Vagif Sultanovich Sultanov, St. Petersburg (RU)

(72) Inventors: Viktor Ivanovich Roschin, St. Petersburg (RU); Vagif Sultanovich Sultanov, St. Petersburg (RU)

(*) Notice: Subject to any disclaimer, the term of this patent is extended or adjusted under 35 U.S.C. 154(b) by 0 days.

This patent is subject to a terminal disclaimer.

(21) Appl. No.: 14/498,034

(22) Filed: Sep. 26, 2014

(65) Prior Publication Data

US 2015/0224065 A1   Aug. 13, 2015

Related U.S. Application Data

(62) Division of application No. 12/601,298, filed as application No. PCT/RU2008/000298 on May 14, 2008, now abandoned.

(30) Foreign Application Priority Data

May 23, 2007 (RU) .................. 2007119231

(51) Int. Cl.
   *A61K 31/045* (2006.01)
(52) U.S. Cl.
   CPC .................. *A61K 31/045* (2013.01)
(58) Field of Classification Search
   None
   See application file for complete search history.

(56) References Cited

U.S. PATENT DOCUMENTS 5,731,357 A * 3/1998 Rubens ............ A61K 31/765
                                                   514/739
2010/0196457 A1   8/2010 Roschin et al.

FOREIGN PATENT DOCUMENTS

EP       0 350 801 B1   4/1995
GB       2310138 A      8/2007
           (Continued)

OTHER PUBLICATIONS

HSC Newsletter Press Release, dated Nov. 14, 2006, downloaded 01122/2012 from the site http:/lwww.health-strategy.com/viewnews.html?id=EEylAZkZZAMbBGYWWyg_&style=Newsletter+P R+View.*

(Continued)

Primary Examiner — Frederick Krass
Assistant Examiner — Michael P Cohen
(74) Attorney, Agent, or Firm — Foley & Lardner LLP

(57) ABSTRACT

The invention relates to the area of the chemical-pharmaceutical industry and medicine, in particular, to an agent for treatment of dependence on ethyl alcohol and/or drugs, treatment of psychosomatic and neurological complications in such patients; to pharmaceutical compositions containing this agent; and to treatment methods for psychosomatic and neurological complications with this agent.

The aim of the invention is to develop a new pharmaceutical agent with minimal side effects.

The proposed therapeutic substance, for treatment of addiction to ethanol and/or drugs, for treatment of psychosomatic and neurological complications in such patients, which is presented by polyprenols of formula (1)

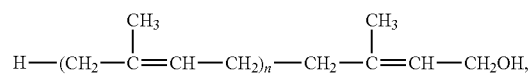

where n=8-20.

Therapeutic composition for treatment of addiction to ethanol and/or drugs, for treatment of psychosomatic and neurological complications in patients is suggested, which includes an effective amount of polyprenols of formula (1)

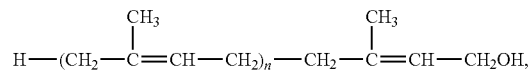

where n=8-20.
and pharmaceutically acceptable excipients, including carriers, and/or solvents. Pharmaceutical composition may be executed in the form of a solution, suspension, capsule, tablet, liposome form.

Attached is the use of polyprenols of formula (1)

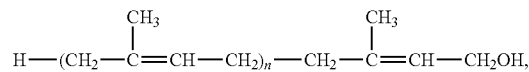

where n=8-20
as an active ingredient of the pharmaceutical composition for treatment of addiction to ethanol and/or drugs, for treatment of psychosomatic and neurological complications in such patients.

Attached is the method of treatment of addiction to ethanol and/or drugs, for treatment of psychosomatic and neurological complications in such patients, which differs in that it includes administration of polyprenols of formula (1).

From the above-mentioned results of the study of the therapeutic substance based on compound of formula (1) conducted in the clinic, one is able to conclude the efficacy of the treatment for addiction to ethyl alcohol and/or drugs, on recovering of abstinence syndrome, and on the improvement of psychosomatic state in patients, as well as on (Continued)

significant improvement of neurological disorders and/or complete regression of polyneuropathy.

It is important to note, that Ropren is well tolerated by patients and side effects, allergic reactions and impairments were not found in any patient in the experimental group for the whole period of treatment.

2 Claims, No Drawings

(56) References Cited

FOREIGN PATENT DOCUMENTS

| LV | 2310138 A | * | 8/1997 | ........... A61K 31/045 |
|----|-----------|---|--------|-------------------------|
| RU | 2137479 C1 | | 9/1999 | |
| RU | 2189231 C1 | | 9/2002 | |
| RU | 225026 C1 | | 5/2005 | |

OTHER PUBLICATIONS

Solagran 2004—Annual Report, downloaded on Jan. 22, 2012 from the site: http://www.solagran.com/images/stories/annual-repoW2004_annual_report.pdf.*

Definition of "Emulsion" from Dictionary.com., downloaded Dec. 1, 2015 from: http://dictionary.reference.com/browse/emulsion.*

Merriam Webster Online dictionary definition of "psychosomatic", downloaded Sep. 1, 2016, from: http://www.merriam-webster.com/dictionary/psychosomatic.*

Killian A Welch. Neurological complications of alcohol and misuse of drugs. Pract Neurol 2011; 11: 206-219.*

International Search Report issued on Sep. 11, 2008 in application No. PCT/RU2008/00298).

Bamba et al., "Separation of Polyprenol and Dolichol by Monolithic Silica Capillary Column Chromatography," Journal of Lipid Research, vol. 46, pp. 2295-2298, 2005.

Fedorow et al., "Dolichol is the major lipid component of human substantia nigra neuromelanin," Journal of Neurochemistry, vol. 92, pp. 990-995, 2005.

HSC Newsletter Press Release, dated Nov. 14, 2006, downloaded Jan. 22, 2012 from the site http://www.health-strategy.com/viewnews.html?id=EEylAZkZZAMbBGYWWyg&style=Newsletter+PR+View.

Solagran 2004 Annual Report, downloaded on Jan. 22, 2012: http://www.solagran.com/images/stories/annual-report/2004_annual_report.pdf.

Office Action issued on Jul. 21, 2011 in U.S. Appl. No. 12/601,298 (US 2010/0196457).

Office Action issued on Feb. 16, 2012 in U.S. Appl. No. 12/601,298 (US 2010/0196457).

Office Action issued on Dec. 5, 2012 in U.S. Appl. No. 12/601,298 (US 2010/0196457).

Office Action issued on Mar. 28, 2014 in U.S. Appl. No. 12/601,298 (US 2010/0196457) 1.

Safatov et al., "Effect of intramuscularly injected polyprenols on influenza virus infection in mice," Antiviral Chemistry & Chemotherapy, vol. 11, No. 3, pp. 239-247, May 2000.

Pronin et al., "Polyprenols as possible factors that determine an instructive role of the innate immunity in the acquired immune response," Russian Journal of Immunology: RJI: Official Journal of Russian Society of Immunology, PUBMED 12687256, vol. 7, No. 2, pp. 135-142, Jul. 2002 (Abstract).

* cited by examiner

AGENT, PHARMACEUTICAL COMPOSITION, AND METHOD FOR TREATING THE ETHYL ALCOHOL AND/OR NARCOTIC DEPENDENCE

TECHNOLOGICAL FIELD

The inventions relate to an area of the chemical-pharmaceutical industry and medicine, in particular to: (i) the agent for treatment of ethyl alcohol and drug dependence and of psychosomatic and neurological complications in such patients; (ii) the pharmaceutical compositions containing this substance; and (iii) to the method of treatment.

Level of Technological Invention

Alcoholism is a gradually progressing disease, which manifests itself via alcohol drug dependence and, typically, neurological, psychiatric and somatic disorders can be observed, along with the occurrence of social conflicts. A syndrome of dependence (as defined the World Health Organization [WHO]) is denoted by a group of symptoms that characterize excessive consumption of alcohol.

In past years, a steady rise in alcohol consumption has been observed in our country, and, in particular, the number of patients suffering from alcoholism has increased. In cases where the amount of alcohol in the blood is 0.04-0.05%, the cerebral cortex is disabled, the person loses control over him or herself, and loses the ability to think rationally. At a blood concentration of 0.1%, the inner areas of the brain that control motor functions are suppressed. Alcohol blood concentrations of 0.6-0.7% can lead to death. The syndrome of alcohol drug dependence presents as an unhealthy desire for alcohol, loss of self-control and alcohol withdrawal syndrome upon abstinence.

The definition of "drug dependence" very clearly reflects the main aspects of the clinical picture of the disease and in the state of the patients: the nature of the patient's existence and state of health is dependant on the presence of alcohol and/or drugs in their bodies or its absence. This dependence affects the mood, state of health, behavior and way of life in general. Alcoholism represents a typical psychiatric problem where it is difficult to determine the causes and mechanisms of the development of the disease.

Although alcohol is the obvious etiological agent, the toxic effect of alcohol and the pathogenesis of the disease can be looked at from different aspects: biological, psychological, socio-cultural and genetic. For this reason, the most well-founded point of view is that alcoholism can be seen as a multifactorial disease, the predisposition to which is determined by hereditary predisposition and influences of the environment.

At present, most significance is given to biological theories, such as the influence of acute and chronic alcohol consumption on the function of neurochemical systems of the brain, including dopamine, serotonin, GABA-ergic and other mediated neurotransmission with corresponding mediators. In the opinion of K., Engel J., Liljequst S. Naunyn. Schmiedebergs Arch. Pharmacol. 1982, October, 321(1), 3-74 and Liljequst S., Engel J., Psychopharmacology (Berl)., 1982, 71-78, alcohol acts on many, possibly all, neurotransmitter systems of the brain. Loss of cholinergic neurons is accompanied not only by the loss of cholinergic function (which characterizes the effect of alcohol), but can facilitate memory loss in alcoholics. The development of abstinence syndrome is characterized by the loss of sensitivity of catecholamine receptors, and changes in GABA-ergic functions can lead to lessening of the convulsive threshold and to commencement of convulsions. Research shows that phosphatase, a mediator of dephosphorylation in NMDA-receptors, plays an important role in passing on the inhibitory effects of ethanol to those receptors. The effect of alcohol on support systems is generally connected to the dopaminergic system At the same time, it is significant that ethanol triggers an increase of dopamine secretion in the n. accumbens, which is modulated by serotonergic and opioidergic systems.

The secretion of dopamine is magnified with the activation of serotonin (5-HT$_3$) receptors and blocking these receptors with administration of ethanol stops the secretion of dopamine. The blocking of µ and/or e-opioid receptors also stalls production of dopamine, which is stimulated by alcohol. That is, the opioid system plays an active part in the development of characteristic disorders of alcoholism. I. P Anohina ("Neuro chemical aspects of pathogenesis of chronic alcoholism" in the book Pathogenesis, the clinic for alcoholism treatment, 1992, pg 15-19) regards that the linkages that form dependence have similarities, no matter which agent causes it (alcohol, morphine and others). The common link in this mechanism is the effect on dopamine mediation in the area of localization of the support systems of the brain. Alcohol evokes an intensive surge of neuromediators into their depots. A large amount of mediator in the synaptic cleft facilities stimulation of the support system, which in many cases determines a positive emotional response. Each time alcohol and/or drugs are used, a new release of the mediator is triggered, leading to a depletion of its reserves, insufficiency of corresponding functions and worsening of the state of health of the patient. These facilitate the yearning for more consumption of alcohol and/or drugs (psychological dependency). However, the additional release of the mediator under the influence of alcohol causes an even greater depletion of mediator reserves in the depot. In a sense, a vicious cycle is created. Later the release of the mediator under the influence of alcohol and/or drugs is facilitated as the result of stress on the compensating mechanisms that define the development of physical dependency on alcohol. When examining the mechanism of alcohol effects, it is important to take into account that it is a membrane-acting lipophilic substance, which is capable of dissolving the lipid layers of membranes, changing the state of receptor complexes on membranes and permeating into nerve cells. These main qualities are connected with alcohol's toxic influence on the CNS.

The concept of reinforcement is one of the leading concepts describing the formation of dependant behaviour. Positive reinforcement and reward is understood as a state that occurs when any kind of stimulus is presented (usually emotionally pleasant, for example, food for a hungry animal) and leads to reinforcement of a behaviour. Negative reinforcement is a state that occurs as a result of the body getting rid of any type of stimulus (usually emotionally unpleasant, dangerous to health). Positive reinforcement is perceived by the individual as a positive emotion. At the present time, scientists have proven that after prolonged use of alcohol, psychomotor stimulants are synthesized in the body: amphetamines, which are located in a particular part of the brain. Fighting the addiction, the attempt to refrain from alcohol and/or drugs, often leads patients into a state of depression. Currently, the role of the insufficiency of central dopaminergic systems in the pathogenesis of depressive conditions is being researched.

The interconnectedness of alcohol and memory impairment has been long proven. There is also a direct connection of alcohol with attention deficit and hyperactive disease symptoms.

It is well known that disintoxication substances are used for treatment of chronic alcoholism. These include magnesium sulphate, thiol substances, intravenous infusion of glucose solution, and infusion of substances like sodium chloride and calcium gluconate that normalize the water-salt balance. Vitamin therapy is widely used for treatment of alcoholism (B group vitamins are prescribed, nicotinic acid in large doses) and also for the relief of abstinence syndrome and for treatment of neurological complications and alcoholic psychosis over 10 days of therapy. Somatic medications are used: coronaroactive substances, substances that improve brain, peripheral and coronary circulation of the blood (such as Gliatilin), hepatotropic and cholagogic substances for hepatitis and cirrhosis of the liver. Sedative and soporific substances are used for relief of abstinence effects and are prescribed for a long duration after the end of abstinence period. The main soporific substances used are the barbiturates. These substances have many contra-indications and have to be used in the given treatment with caution because they are synergists to alcohol. Alcoholic patients display a cross-tolerance to them, thus the soporific effect is only present when a dose of 2-3 times above the regular therapeutic dose is administered.

This aside, it is well known that in the treatment of alcoholism psychotropic substances are widely used: tranquillisers and neuroleptics (Fenezipam, Metakvalon, Sibazon, Levomepromazin, Aminazin, Rezeprinetaperezin, Galoperiodol and others). The tranquillisers used are, in general, the benzodiazepines (seduxen, diazepam, seduxen, relanium), chlozepidum (elenium, Napoton), nozepam (tazepam, oxazepam), Phonozepan and others. However, all these therapeutic substances have a range of contra-indications. They cause addiction in the patients to these substances in addition to other types of dependence—medicinal dependency to the substances and an unhealthy addiction known as toxicomania. Tranquillisers also cause athenia, flatness, drowsiness, apathy and depression. Many therapeutic substances support the development of side-effects during psychosomatic state in patients. For instance, ethaperezin (trilaphon) can cause extrapyramidal disorders, in the form of increased muscle tone, tremors and convulsions. Neuroleptics, to which haloperidol is related, are widely used to relieve symptoms of abstinence, psychomotor agitation and the accompanying psychosis in alcoholics, and can lead to a range of undesirable CNS after effects, such as extrapyramidal consequences (for instance parkinsonism, hyperkinesias and dystonia). Therapy with neuroleptics leads to medicinal Parkinsonism and hyperkinetic and dyskinetic syndromes are also observed.

Besides that, all these synthetic substances have a toxic effect on the liver and pancreas; many are contraindicative to hepatitis, cirrhosis of the liver, the pancreatitis which often accompanies chronic alcoholism, hypertension, disruption to blood circulation in the brain, cardiovascular diseases, and ulcers of the gastrointestinal tract. The course of treatment is usually lengthy and can lead to a variety of complications which can extend to memory impairment.

In patent SU 629926, application WO99/17779 describes the use of substances of different groups: vitamins, nootropics, neuroleptics, anti-depressants, lithium substances, and derivatives of phenylalkylamine, benzodiazepine for the treatment of addiction to ethyl alcohol and/or drugs and for the treatment of psychosomatic and neurological complications in alcoholics and/or drug addicts.

Application WO96/35425 can be regarded as the closest analogue, which describes treatment for alcohol dependence using inhibitors of monoamine oxidase (MAO). The shortcomings of this treatment method are typical of treatments using inhibitors MAO: undesirable side-effects on the liver, considering that the liver is frequently damage in alcoholics.

INVENTION

The purpose of the invention is to create a new substance and method of treatment of ethyl alcohol and/or drug dependence and for treatment of psychosomatic and neurological complications in alcoholics and/or drug addicts, free of the above-listed shortcomings. The purpose is to also search for new therapeutic substances with minimal side-effects, which presently is a problem in the treatment of similar diseases.

The presented tasks will be solved as follows.

The proposed therapeutic substance, for treatment of addiction to ethanol and/or drugs and for treatment of psychosomatic and neurological complications in such patients, presented by polyprenols of formula (1)

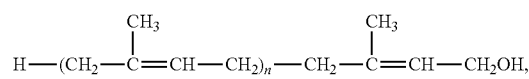

where n=8-20.

The therapeutic composition for the treatment of addiction to ethanol and/or drugs and for the treatment of psychosomatic and neurological complications in patients is suggested, which includes an effective number of polyprenols of formula (1)

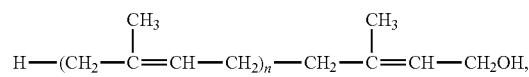

where n=8-20.

and pharmaceutically acceptable excipients, including carriers, and/or solvents. The pharmaceutical composition may be executed in the form of a solution, suspension, capsule, tablet, liposome form.

Attached is the use of polyprenols of formula (1)

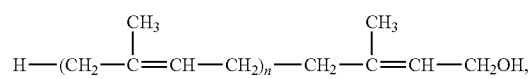

where n=8-20.

as an active ingredient of the pharmaceutical composition for treatment of addiction to ethanol and/or drugs, for treatment of psychosomatic and neurological complications in such patients.

Attached is the method of treatment of addiction to ethanol and/or drugs, for treatment of psychosomatic and neurological complications in such patients, which differs in that it includes administration of polyprenols of formula (1)

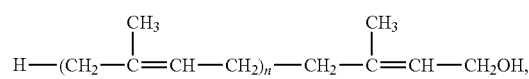

where n=8-20.

The search for a new treatment that could slow down the process of neuronal cell death or to allow identification of level of reversibility of the clinical presentation of the severe course of chronic alcoholism (drug addiction) displaying encephalopolyneuropathy, psychoses and weak-mindedness have led us to use plant origin polyprenols of formula (1) in psychiatric practice. In the treatment of given pathologies, plant origin substances are most favourable because of their decreased toxicity (taking into account liver and kidney damage in all patients with the given nosological form), the possibility of prolonged use and the reduction of the side effects of psychotropic substances.

Polyprenols of formula (1) is a natural mix of oligomers (isoprenols), called Ropren, acting as one substance, but able to be divided into individual isoprenols using reverse phase sorbents. Ropren is derived from green coniferous species (patent RU2017782).

This polyprenol has been shown to have an anti-ulcer effect (N. A. Skuya and others) Products of processing of green verdure—perspective of using in gastroenterology: "Functional diagnostics and efficacy of treatment of diseases of digestive apparatus", Vilnuis, 1988, part 4, pg. 675-676), hepatoprotector (U.S. Pat. No. 5,731,357), immunomodulating (patent RU2137479).

It is preferable to obtain a more pure fraction of isoprenols—Ropren, by a method described in patent RU2238291. The method is based on the extraction from tree verdure of coniferous and deciduous species with organic solvent, separation of coniferous wax by settling and filtration while cooling, separating free oxides from the thus obtained solution of extractive substances by alkali solution action, dividing the obtained neutralized solution into a neutral substance solution in the hydrocarbon solvent and a water-alkali solution of organic acid salts. The solvent is isolated form the neutral substance solution. The neutral substances are subsequently extracted with acetone and $C_1$-$C_3$ alcohol. Mass ratio "neutral substances—extractant agent" from 1:2 to 1:5 is used in the acetone treatment. The neutral substance that is insoluble in acetone is made up of: concentrates of higher fatty acid esters that are produced in association with triterpene alcohol, stearins, higher fatty alcohols and an acetone-soluble residue. The residue is isolated from the acetone and the residue is treated with ethanol. By treating the remainder with alcohol, the total diterpene alcohols are separated from the polyprenol acetates, which are insoluble in alcohol. Saponification of the polyprenol acetates with alcoholic alkali solution results in obtaining polyprenols concentrate. These polyprenols, with density 0.893-0.897 g/ml, are obtained by using chromatography of stated concentration on silica gel with a substance:sorbent at ration of 1:10, using hexane, and hexane with addition of 5% and 10% of diethyl ether with sorbent-solvent ration of 1:2. HPLC chromatogram should show peaks with a shape and location typical for polyprenol of formula (1) chromatogram. Chromatography set-up: 3.0×150 mm column filled with extracting agent octadecyl silica gel of X-Terra $C_{18}$ type or similar; mobile phase—acetone-methanol mixture (80:20); flow rate—1 ml/min.

If it is necessary to obtain dry matter, the concentrate of polyprenols is subjected to cool dehumidification.

The basis for the application of polyprenol compound of formula (1) for the applied claim was identification of new activities, which were previously unknown for this compound.

Ropren can serve as an exogenous source of isoprenoid links, out of which an endogenous product, dolichol, is created in the body. Isoprenoid links (out of which Ropren is produced) can be used by the body both for cholesterol formation and for ubiquinone production, which are vital metabolites. Ropren, which belongs to exogenic isoprenoids, may prove to be an effective drug for treatment of different types of psychiatric conditions as well as alcoholism. Numerous studies have shown that alcohol affects the metabolism of dolichol. In the blood and in urine its levels in alcoholics are significantly raised, which is a bioindicator of chronic alcoholics (patent U.S. Pat. No. 5,747,346).

Presently, there are data proving that one of the lipids contained in the myelin sheath of nerves is dolichol. Dolichol was found in brain's black matter, in the neuromelanin and its content was quiet high, up to 15% (Joshida K., Engel J., Liljequst S. Naunyn. Schmiedebergs Arch. Pharmacol. 1982, October, 321(1), 3-74, Investigation of lipid component of neuromelani (NM). Usually, protein is dominant in the composition of membranes, but in the case of myelinated nerve membrane, three quarters of the mass is comprised of lipids. In cases of alcoholism, a toxic dysmetabolic encephalopathy develops, which is related to metabolic disorders and disorders of peripheral functions of the nervous system, where myelinated nerve fibers are damaged. In this case Ropren may prove effective for restoring of the myelin nerve membranes that are toxically damaged with alcohol and/or drugs or other damaging factors. It can also be assumed that Ropren, being made up of isoprene links like dolichol, displays membrane-active properties that effect the fluidity and viscosity of the membranes. It seems that bonding of the polyisoprenoid fragment at its α-terminal with glycoproteins, and subsequently with protein, facilitates protein or peptide transport and transmission of nerve impulses even without damaging the myelinated fibres and without pathological processes in the body It is known that alcohol affects the dopamine receptors, inhibiting them and leading to depression. The nigrostrial area of the brain regulates the dopaminergic transmission of nerve impulses. Insufficiency of the dopaminagenic nigrostrial system is a deregulating mechanism that leads to dopamine dependant depressive syndrome. In particular dolichol was found in the nigrostrial system of the brain (or substantia nigra), however it is still unclear what function it performs. (N. A. Krupina, G. N. Kryzhanovskyi). Insufficiency of the dopaminagenic nigrostrial system is a deregulating mechanism that leads to dopamine dependant depressive syndrome. Neurological psychiatry, 2002, 103 No 4, pg. 42-47)

Earlier research conducted on the therapeutic properties of Ropren showed that the most pronounced therapeutic effect of the Ropren treatment was obtained in patients with the combined pathology of cranio-cerebral trauma and alcoholism with a background of vascular dementia. There were improvements in psychological condition by 9-15 points (on average) as per the MMSE scale and improvement of biochemical parameters of blood, as well as positive changes in encephalography (EEG). Also, an improvement of the patient's general condition and a reduction of anxiety-depression and hypochondriac syndromes was noted. It was established that Ropren has a normalizing effect on the enzymes butyrylcholinesterase (BuChE—marker of AD) and monoamine oxidase (MAO—marker of depressive state), which led us to the conclusion that Ropren has a modulating effect on enzyme activities, which perform the function of neuromediators and participate in the cholinergic transmission of neurons. Thus, Ropren has a positive effect in treating the given pathological conditions.

The I.M. Sechenov Institute of Evolutionary Physiology and Biochemistry conducted experiments on animals to study the effect of Ropren on different areas of the brain. In cases of toxic damage of the body caused by carbon tetrachloride, it has been established that the drug has a protective and regenerative effect in different parts of the brain: in the striatum, hypothalamus and medulla. The effect of Ropren is considered to be related to participation of the drug in repair processes of damaged membranes, as well as in processes of enzyme transformation caused by changes in the viscosity of the lipid bilayer of mitochondrial membranes in the brain.

Based on the literature and experimental data, it can be assumed that the polyprenols of the formula (1) display membrane-active properties that affect the fluidity and viscosity of membranes, as well as the processes of transforming the enzymes by changing the viscosity of the lipid bilayer of mitochondrial membranes in the brain. They may prove to be very promising for the treatment of chronic alcoholism and/or drug addiction (in particular for treatment of one of the manifestations, encephalopolyneuropathy).

Pathogenesis of alcoholism and/or drug addiction is a difficult multifactorial process. The complex structure of this process is represented by both general neurodynamic disorders and localized and more specifically systemic neurodynamic disorders in the form of a powerful complex of pathological conditional and unconditional reflexes to alcohol (drugs). In its entirety, this complex makes up the dominant alcohol and/or drug dependance, in the pathophysiological sense of the word, in the patient. Furthermore, the clinical picture of alcoholism (drug addiction) depicts different degrees of severity of chronic psychiatric disorders (psychopathy-like state, sensory decline, weak-mindedness), as well as numerous somatic-neurological complications.

In cases of alcoholism and/or drug dependence, neurological disorders may manifest themselves as disorders of vegetative nervous regulation and a variety of symptoms of nervous system damage to give rise to polyneuropathy. In the later stages of developing dependence, a significant loss of tendinous reflexes is observed and even their complete absence (development of polyneuritis). Skin reflexes (abdominal, cremasteric) are usually heightened, however sometimes lowered and even absent. In the state of sobriety, often pathological reflexes in the face are activated: reflexes of the oral automatism, Marinesco symptom, a static (stagger in Romberg's pose) ataxia and, less often, dynamic ataxia is noted. Taking into account the damage to nerve fibres in cases of chronic alcoholism and the development of the so-called alcoholic encephalopolyneuropathy, after a couple of years the authors discovered that Ropren can be effective not only as a hepatoprotector in its direct application in the case of chronic alcoholism, and the liver damage associated with it (RU 2252026), but also as a substance that improves the transmission of nerve impulses in cases of damaged myelinated fibres for the treatment of polyneuritis and various paresis in alcoholics and/or drug addicts.

Examples of Proffered Execution of the Invention

In the treatment of alcoholism and/or drug addiction, it is very important to start the treatment as early as possible. Patients in the first stages of the disease require treatment as well as those who have already formed the symptoms of dependence. The treatment has to be continuous and lengthy, and possibly more individualised, as well as composite and pathogenetically founded. It is imperative to have continuity in the treatment and the aim should be not only the abstinence from alcohol and/or drugs, but also the forming of active adjustment in the patient with the conscious refusal to consume alcohol and/or drugs in any form. The treatment of each patient involves the following goals:

1—elimination of any damage to the psychiatric and somatic sphere caused by alcohol and/or drug abuse,
2—suppression of unhealthy attraction to alcohol and/or drugs,
3—support for the purpose for an alcohol-free (drug-free) lifestyle, social support.

In one course of therapy these goals are subdivided into 3 stages. The first stage includes relief from the acute effects of alcohol intoxication and abstinence, normalizing of mental states (affected states, different types of neurosis, depression, neurological disorders) and intensive therapy directed at elimination of abnormalities of a metabolic nature of the central nervous system (CNS), cardiovascular system and digestion. The second stage assumes active anti-alcohol therapy that is directed at suppressing an unhealthy attraction to alcohol, the development of aversion, including an aversion to drugs etc. Symptomatic and somaneurological therapies continue at this stage. The third stage is to enable a psychotherapeutic effect, which is directed at the change of lifestyle.

Administration of polyprenols of formula (1) to the patients can be as the pure substance, or as a part of pharmaceutical composition in combination with pharmaceutically acceptable carriers, solvents and excipients.

The effective amount, as per the claimed use, is within the range from 1 to 150 mg and can be administered in the form of a single or several doses per day. More specific doses depend on the type of pathology, the patient's condition, the presence of accompanying diseases, as selection of doses and duration of treatment are strictly individualised.

Examples of pharmaceutical compositions include any solid (such as tablets, pills, capsules, granules, etc.) or liquid (such as solutions, suspensions, emulsions) therapeutic forms for internal administration, traditional forms for parenteral administration or for rectal administration (such as suppositories).

Compositions for oral administration can contain traditional excipients; they can be prepared in solid or liquid forms: tablets, capsules, solutions, suspensions or syrup; they can contain any acceptable excipients such as: binding agents (eg sugar, gelatin, sorbitol, tragacanth, polyvinylpyrrolidone), diluents/fillers (eg lactose, sugar, starch, calcium phosphate, sorbitol), tablet lubricants (eg magnesium stearate), disintegrants (eg starch, polyvinylpyrrolidone, microcrystalline cellulose, carboxymethyl cellulose), humidifiers (eg sodium lauryl sulphate), dispersing surface-active substances. Liquid forms for oral administration can include solvents (eg water, vegetable or animal oils), dextrose and other solutions of saccharides, glycols, dispersing surface-active substances (SAS). The mentioned compositions are prepared using traditional and conventional methods. These methods include mixing of active ingredients with carrier, which can include one or more excipients, and obtaining a finished product from the mixture.

Tablets can be obtained by compression, using special equipment. In this case an active ingredient is mixed, if necessary, with binding agents (eg povidone, gelatin, hydroxypropylmethylcellulose), diluents/fillers, lubricants, inert solvents, disintegrants (such as cellulose derivatives, cross-linked povidone, sodium carboxymethyl cellulose), surfactants or dispersing agents. Tablets, obtained by molding using the appropriate equipment, contain a mixture of wetted powder compound of formula (1) with inert liquid solvents. If necessary, tablets can be coated for slow or controlled release of active ingredient. Coating can be obtained, for instance, from excipients such as hydroxypropyl starch, dibasic sodium phosphate or hydroxypropylmethylcellulose or its mixture with gelling agents (such as gelatine, waxes) at different ratios for obtaining the preferred release profile.

Composition for parenteral administration can be prepared by both traditional pharmaceutical methods (solutions, suspensions), and in a form of water micro-emulsions (as per patent RU 2189231) based on Hanks solution with 10% of ethanol or by other methods. They can include water, pharmaceutically acceptable fats or oils, alcohols or other organic solvents, surfactants and/or antioxidants, preservatives. Normal concentrations of the compound of formula (1) are within the range from 0.1% to 80%. Finished compositions can contain a single dose or be produced in a form of ampoules or vials, which contain several single doses. If necessary, finished therapeutic forms can contain stabilizers, buffer systems, and other excipients.

Agents for rectal administration can include those traditional for these forms of substances, such as paraffin, vegetable, animal or mineral fats or oils, emulsifiers, polyethylene glycol, lauryl sulfate or sulfate salts, or sodium hydrogen carbonate.

Parameters of pharmaceutical composition.
Liquid Peroral Form.
It contains the following components, weight %

| | |
|---|---|
| The compound of formula (1) | 10.0-60.0 |
| Sunflower oil | remainder to 100.0 |

Below are examples 1 and 2 of possible compositions for the liquid therapeutic form of the substance.

EXAMPLE 1

| | |
|---|---|
| The compound of formula (1) | 25.0 |
| Sodium ascorbate | 0.1 |
| Vitamin $B_6$ + $B_{12}$ | 0.1 |
| Sunflower oil | remainder. |

EXAMPLE 2

| | |
|---|---|
| The compound of formula (1) | 25.0 |
| Essential phospholipids | 25.0 |
| Sunflower oil | remainder. |

The compound of formula (1) and sunflower oil are mixed together, and with other ingredients (if present) in the above-mentioned proportion, then the mixture is dispensed into vials with a doser and sterilised.

EXAMPLE 3

Suspension for parenteral administration. It contains the following components, weight %

| | |
|---|---|
| The compound of formula (1) | 20 |
| Tween 80 | 25.0 |
| Ethanol | 4.0 |
| Polypropylene glycol | 10.0 |
| Pyrogen-free water | remainder. |

The compound of formula (1) is mixed with ethanol, polypropylene glycol, then heated water is added and thoroughly stirred; the mixture is dispensed into ampoules and sterilised.

EXAMPLE 4

Gelatin Capsules Capsules Contain the Following Components, Weight %

| | |
|---|---|
| The compound of formula (1) | 46.0 |
| Copolymer of methacrylic acid | 12.0 |
| Talc | 5.7 |
| Copolymer of methacrylic and acrylic acids | 18.0 |
| Glycerol triacetate | 3.3 |
| Magnesium stearate | 15.0 |

EXAMPLE 5

Gelatin Capsules

| | |
|---|---|
| Weight of the capsules | 238-262 mg (100%) |
| The compound of formula (1) | 20.0 weight % of capsule's weight |

EXAMPLE 6

Gelatin Capsules

| | |
|---|---|
| Weight of the capsules | 240-260 mg (100%) |
| The compound of formula (1) | 6.0 weight % of capsule's weight |
| Sunflower oil | 14.0 weight % of capsule's weight |

EXAMPLE 7

Gelatin Capsules

| | |
|---|---|
| Weight of the capsules | 240-260 mg (100%) |
| The compound of formula (1) | 4.0 weight % of capsule's weight |
| Sunflower oil | 16.0 weight % of capsule's weight |

EXAMPLE 8

Gelatin Capsules

| | |
|---|---|
| Weight of the capsules | 412-420 mg (100%) |
| The compound of formula (1) | 48.0 ± 0.5 weight % of capsule's weight |

EXAMPLE 9

Gelatin Capsules

| | |
|---|---|
| Weight of the capsules | 412-420 mg (100%) |
| The compound of formula (1) | 2.4 ± 0.1 weight % of capsule's weight |
| Sunflower oil | 47.0 ± 0.2 weight % of capsule's weight |
| Sodium ascorbate | 0.1 weight % of capsule's weight |
| Vitamin $B_6 + B_{12}$ | 0.1 weight % of capsule's weight |

EXAMPLE 10

Gelatin Capsules

| | |
|---|---|
| Weight of the capsules | 412-420 mg (100%) |
| The compound of formula (1) | 10.0 ± 0.2 weight % of capsule's weight |
| Sodium ascorbate | 0.1 weight % of capsule's weight |
| Vitamin $B_6 + B_{12}$ | 0.1 weight % of capsule's weight |

EXAMPLE 11

Gelatin Capsules

| | |
|---|---|
| Weight of the capsules | 208-212 mg (100%) |
| The compound of formula (1) | 24.0 ± 0.2 weight % of capsule's weight |

EXAMPLE 12

Gelatin Capsules

| | |
|---|---|
| Weight of the capsules | 208-212 mg (100%) |
| The compound of formula (1) | 5.0 ± 0.1 weight % of capsule's weight |
| Sunflower oil | 19.0 ± 0.2 weight % of capsule's weight |

Capsules that are mentioned in the examples 4-12 do not contain components of animal origin. The compound of formula (1) is mixed with vegetable oils or in the mixture with oil in the above proportions, then placed into the apparatus to obtain the therapeutic form. Then, the capsules are dried to 3-5% water content at a temperature not exceeding 45° C.

EXAMPLE 13

Liquid liposomal form of the substance. It contains the following components, weight %

| | |
|---|---|
| The compound of formula (1) | 0.4 |
| Lecithin | 4.0 |
| Preservative | 0.001-0.2 |
| Water | remainder. |

The liposomal form was prepared using the method of mechanical emulsification in liquid phase from soy-bean lecithin, which was subjected to additional purification. The compound of formula (1) was added to a composition of lipids in chloroform solution with further evaporation, with the subsequent addition of water and emulsification.

Studies were conducted to research the therapeutic efficacy of Ropren in cases of chronic alcoholism (drug addiction) and to research the after-effects related to this disease. A comparison was made between Ropren therapy and base therapy for treatment of chronic alcoholism. The safety of Ropren in treating of the above-mentioned diseases and/or states and their side-effects was also examined.

Clinical trials of the product, which were conducted in Russia on base of St. Petersburg's municipal institutions: "St Georgiy Hospital", Botkin's hospital No. 30, 1 and 2 therapeutic unit of clinics of Medical Academy Postgraduate Education, Centre for prophylactics and treatment of AIDs and infectious diseases, revealed that the product is safe and effective. Furthermore, clinical tests of the therapeutic substance were conducted at the "Scvortsov-Stepanov Municipal psychiatric hospital No 3 (Saint-Petersburg). The effect of the therapeutic substance Ropren was assessed in regards to the development of complications after alcohol and drug poisoning, and the psychiatric and neurological status of the patient before and after treatment with the substance (psychiatric and neurological disorders, change in biochemical blood indices and EEG data).

Assessment was conducted by the method of neurological and psychiatric control taking into account the anamnesis of the patient, with the use of scales ("symptom list", HADS scale, Young scale) and EEG data. As EEG epicomplexes are often registered in patients with alcoholism, the study completed electronic data processing of EEGs, allowing tracking of rhythm changes in the presence of epiactivity in the brain. The effect of the therapeutic substance Ropren was assessed in the accompanying disorders associated with alcoholism: polyneuritis of the extremities before and after treatment (on Young's scale), as well as on the dynamic of epileptic fits and Parkinson's syndrome.

The diagnosis of the disease was established on the grounds of the anamnesis of the disease of each patient taken by the psychiatric doctor, the neurologist and the doctor of functional diagnostics of EEG data. Diagnostics of the patients was performed by using screening scales, which allow for evaluation of severity of a disease and a stage of the pathological process, as well as the evaluation of the effect of the new drug.

Important information was given by the paraclinical examinations, which included EEG, biochemical blood analysis, hepatic enzymes, clinical blood and urine analysis. On the basis of all this data patients were sorted and the following diagnosis was given: "Chronic Alcoholism $2^{nd}$ stage, drug addiction". To evaluate the general state of the patient, the emotional background and social skills of the patients before and after treatment along with the following examinations and methods were used:

The patients underwent clinical psychiatric examination using a semi-structured interview method. The method for assessing the emotional background was the international hospital anxiety and depression scale, HADS (Andrushenko A. V. and others. The comparative evaluation of scales CES-D, BDI, HADS (d) in diagnosis of depression and general medical practice, Journal Neurology, Psychiatry. 1997, No 9, pg. 60-81). This was assessed before and after treatment. For interpretation of the data on this scale, a summary index for each scale (A—anxiety, D—depression) is considered. At the same time, 3 significant ranges are identified: 0-7 points is described as "the norm"; 8-10 points is described as "sub-clinically expressed anxiety/depression"; 11 points and above is described as "clinically expressed anxiety/depression". Evaluation of somatic-autonomic conditions using a "list of symptoms" questionnaire was conducted before and after treatment.

Patients were examined by a psychiatrist and neurologist before the start of therapy, after 15 days of therapy and after completion of therapy (30 days). For assessing the medical efficacy of the therapy, EEG was conducted using standard methods in the control and the experimental group to establish the pattern of brain function in the given state before and after treatment. Constant time (0.3 seconds) and high-frequency bandwidth (30 Hz) was used. Nineteen electrodes were located as per the international scheme "10-20". The averaged method was used to establish the bio-potential lead. For the averaged electrode (Av), a sum of the potential of all active electrodes was used, dividing it by their amount. Averaged ear electrode served as a silent electrode. In the duration of 2 minutes a registration of EEG was conducted in a calm/awake state with eyes closed, thereafter a test was conducted with opening and closing of eyes, rhythmic photostimulation (RPS) and two minute hyperventilation. RPS was conducted discretely in the range of frequencies from 2 to 35 Hz with interval of 2 Hz (importance of flare—0.3 joule, duration 50 microseconds). Each frequency was transmitted in the duration of 5-6 seconds; the pause between stimulations was 1-12 seconds.

For assessment of the brain's functional state a method by Pavorinskyi A. G., Zabolotnyh V. A, (Textbook for clinical encephalography, 1987) was used. The visual analysis of EEG consisted of evaluating the percentage content (indices) of rhythms, the expression of reaction of the driving rhythm in points and the expression of bio-electrical activity of the brain in points. On the basis of this, a type of EEG is determined by classification as presented by I. A. Svyatogor. Besides the visual analysis of EEG, we have also used the spectral method of assessing bio-electrical activity.

For quantitative evaluation of tactile, pain, thermal and vibration sensitivity thresholds, points were applied to each level of disorder (from 0 to 5 points). In order to transfer disorder of human papillomavirus to NDS (Neuropathy Disability Score) conditional points, a special algorithm was developed: reflex disorders were expressed in points (from 0-2 points). The sum of mean values for each type of sensitivity at two extremities and sum of the values for each of 4 reflexes—full scale of HADS was composed (Young M. J., 1993).

Clinical characteristic of patients in control and experimental groups before treatment is presented in Table 1.

TABLE 1

| Parameters of patients | Control group, n = 30 people | Experimental group, n = 60 people |
|---|---|---|
| Age of patients | 62.83 ± 13.89 | 56 ± 13.0 |
| Men:Women | 27:3 (9:1) | 47:13 (3.6:1) |
| Average duration of disease | 9.8 ± 1.97 | 9.9 ± 1.69 |
| Duration of disease: | | |
| up to 5 years | 36.7% | 31.7% |
| 6-10 years | 43.3% | 45.0% |
| exceeding 10 years | 20% | 23.3% |
| Number of patients with pneumonia | 23.3% | 11.7% |
| Number of patients with hepatitis "B", "C" | 30.0% | 33.3% |
| Number of patients taking drugs (heroin, opium) | 3.3% | 13.3% |
| Number of patients being HIV-infected | 3.3% | 11.7% |
| Number of patients with type 2 diabetes | 13.3% | 5% |

TABLE 1-continued

| Parameters of patients | Control group, n = 30 people | Experimental group, n = 60 people |
|---|---|---|
| Number of patients with convulsive disorder | 10.0% | 20% |
| Number of patients with acute alcohol syndrome | 3.3% | 5% |
| Number of patients with acute alcohol induced suicidal state | 3.3% | 5% |
| Number of patients with coronary disease and type 2 of hypertension | 23.3% | 5% |
| Number of patients with toxicomania and poisoning | — | 6.7% |
| Number of people with oncological problems | — | 1.7% |
| Number of patients with craniocerebral injury | — | 3.3% |
| Number of patients with Korsakoff's amnestic syndrome | — | 3.3% |
| Number of patients with secondary syphilis | — | 3.3% |
| Number of patients schizophrenia | — | 5% |
| Number of patients with obesity of 3-4 level | — | 3.3% |
| Number of patients with tick-borne encephalitis | — | 1.7% |

Methods of treatment for the experimental group of patients included administration of infusive liquids, physiological solution, and glucose at a dose from 1.0-2.5 liters per day, subsequent dehydration a diuretic agent and administration of Ropren instead of B group vitamins at dose of 8 drops, 3 times daily (in the form of oil solution) before food for one month.

Experimental group of patients did not receive treatment with nootropic drugs, B group vitamin and cerebroprotectors (only the control group received these drugs).

As a result of the therapy with compound of formula (1), distinct positive changes were achieved in relation to psychosomatic and neurological symptoms for both the frequency of the symptoms and for the degree of their expression (depth). In particular, there was marked improvement in general condition (subjective and objective), and disappearance of anxiety, depressive and hypochondriac complaints in patients that were treated with Ropren. The high efficacy of the substances activity was noted in relation to treatment of psychosomatic complications. The parameters of the psychosomatic state of patients are presented, as per the HADS scale and the questionnaire "list of symptoms" (Table 3).

Changes in the psychosomatic state of patients who suffer from chronic alcoholism in experimental and control groups before and after treatment with Ropren in accordance with the hospital anxiety/depression scale (HADS) is shown in Table 2.

TABLE 2

| Patient parameters | Experimental group of patients n = 60 people | | Control group of patients n = 30 people | |
| --- | --- | --- | --- | --- |
| | Before treatment | After treatment | Before treatment | After treatment |
| Age of patients | from 17-74 y.o., average 56 ± 13 | | From 25-83 y.o., average 62.83 ± 13.89 | |
| Men:Women | 47:13 | | 27:3 | |
| Duration of disease | from 3-20 years | | from 3-20 years | |
| Evaluation of severity of anxiety/depression in points using HADS scale, in % | | | | |
| Absence of depression, standard (0-5 points) | | 80% (48 people) | | 55.2% (16 people) |
| Subclinically expressed form of anxiety/depression (6-10 points) | | 16.7% (10 people) | | 41.3% (12 people) |
| Clinically expressed form of anxiety/depression (11 points and more) | 100% (60 people) | 3.3% (2 people) | 100% (29 people) | 3.5% (1 person) |

Changes in psychosomatic state of patients who suffer from chronic alcoholism in experimental and control groups before and after treatment with Ropren, assessed by questionnaire "list of symptoms" is shown in Table 3.

TABLE 3

| Patient parameters | Experimental group of patients n = 60 people | | Control group of patients n = 30 people | |
| --- | --- | --- | --- | --- |
| | Before treatment | After treatment | Before treatment | After treatment |
| Age of patient | from 17-74 y.o., average 56 ± 13 | | From 25-83 y.o., average 62.83 ± 13.89 | |
| Men:Women | 47:13 | | 27:3 | |
| Duration of disease | from 3-20 years | | from 3-20 years | |
| Evaluation of severity of anxiety/depression in points using questionnaire "list of symptoms", in % | | | | |
| Absence of depression, standard (0-5 points) | | 75.0% (45 person) | | 37.9% (11 people) |
| Depression remains (6 points and more) | 100% (60 people) | 25% (15 person) | 100% (29 people) | 62.1% (18 person) |

Tables 2 and 3 show that a clear improvement occurs in the psychic state of patients.

After treatment with Ropren in the experimental group using questionnaire, "list of symptoms":
An improvement, no signs of depression, was found in 75% of patients,
Depression remained in 25% of patients,
Improvement occurred, without any remaining signs of depression (using scale HADS) in 80% of patients
Depression remained in 20% of patients.

On average, after 3-6 days of treatment, these patients started to report improvement in their condition, with statements as follows: "feel much better . . . my head is clearer . . . I feel like I can do things . . . " etc. The disturbing feelings of internal pressure, anxiety and unpleasant somatic feelings in the patients disappeared. Expressed improvement in mood was registered in 90% of cases, with some euphoric tone. In 80% of the patients, disappearance of headaches, dizziness and loss of coordination while walking, numbness of limbs and body tremors was noted.

The general somatic condition of the patients improved significantly. Whinging, irritability, predisposition to loose temper was reduced, while sleep was normalised. Psychotic symptoms improved without the use of antidepressants in six patients with anxiety-depressive symptoms. Therefore, Ropren manifests an efficacy in treatment of alcohol abstinence syndrome on a background of chronic alcoholism and/or drug addiction which is expressed as a reduction of depression and abstinence syndrome.

High efficacy of the substance was identified in relation to neurological complications of focal cerebral symptoms and polyneuropathy (PNP).

Changes in the brains focal and cerebellar pyramidal symptoms were identified in patients' anamnesis. Neurological state was evaluated before therapy, on $15^{th}$ day and at the end of the course on the $30^{th}$ day (±2-3 days) (Table 4). A 5-point system was used for evaluation of efficacy of the treatment: significant improvement (1 point), improvement (2 points), some improvement (3 points), without any effect (4 points), impairment (5 points).

TABLE 4

Changes in neurological state (focal cerebral symptoms)

| No | Improvement rate | Control group of patients (n = 30) | Experimental group of patients (n = 60) |
|---|---|---|---|
| 1 | Significant improvement | 10% (3 person) | 49.2% (29 people) |
| 2 | Improvement | 26.7% (8 person) | 32.2 (19 people) |
| 3 | Some improvement | 43.3% (13 people) | 15.2% (9 people) |
| 4 | Without any effect | 13.3% (4 people) | 1.7% (1 people) |
| 5 | Impairment | 6.7% (2 people) | 1.7% (1 person) |

Table 4 shows significantly more evident and expressed improvement of focal cerebral symptoms after treatment with Ropren compared to the control group. In more than 90% of the cases, chronic use of alcohol causes polyneuropathy (PNP), which is expressed in paresthesia and numbness of limbs, pain, burning, reduction in reflexes, reduction in pain threshold of vibratory, thermal, tactile sensation of hands and legs limbs. (Trinitatsky Yu. V., Trinitatsky I. Yu. Treatment of chronic demyelinating polyneuropathies, State Medical University, Rostov-na-Donu, 2003, p. 176). Alcohol polyneuritis is a primary degenerative process with breakdown of myelin, axis cylinders and replacing of nerve tissue with connecting vessel-rich tissue. Motor nerves are affected in the first place, with radial nerves in the upper limbs and perineal nerves in the lower limbs being the first affected. Pectoral and phrenic nerves are involved in pathological processes. The visual nerve of the retina is often damaged. Almost all patients examined by a neurologist had a diagnosis of toxic encephalopathy. In the control group, 86.2% (25 people) of patients had a diagnosis of polyneuropathy, while in the experimental group, 95% (57 people out of 60 examined).

Table 5 shows characteristics of patients with polyneuropathy in the control group before and after treatment using basic therapy and assessed according to Young's scale.

TABLE 5

| Patient parameters | Before treatment | After treatment | |
|---|---|---|---|
| | | After 15 days | After 30 days |
| Age | from 25-83 y.o. | | |
| Men:Women | 26:3 | | |
| Duration of disease | from 3-20 years | | |
| Evaluation of severity of neuropathy in accordance to Young's scale, in % | | | |
| Moderate form (3-5 points) | 13.8 (4 people) | 17.3 (5 people) | 34.5 (10 people) |
| Expressed form (6-8 points) | 44.8 (13 people) | 48.3 (14 people) | 48.3 (14 people) |
| Severe form (9-10 points) | 27.6 (8 people) | 20.7 (6 people) | 3.4 (1 person) |
| PNP was not registered | 13.8 (4 people) | 13.8 (4 people) | 13.8 (4 people) |
| Norm (recovered) | None | None | None |

Table 5 shows characteristics of patients with polyneuropathy in the experimental group before and after treatment using Ropren and assessed according to Young's scale.

TABLE 6

| Patient parameters | Before treatment | After treatment | |
|---|---|---|---|
| | | After 15 days | After 30 days |
| Age | from 17 to 74 y.o. | | |
| Men:Women | 47:13 | | |
| Duration of disease | from 3-20 years | | |
| Evaluation of severity of neuropathy in accordance to Young's scale, in % | | | |
| Moderate form (3-5 points) | 23.3 (14 people) | 58.4 (35 people) | 76.6 (46 people) |
| Expressed form (6-8 points) | 45.0 (27 people) | 33.3 (20 people) | 8.4 (5 people) |
| Severe form (9-10 points) | 26.7 (16 people) | 3.3 (2 people) | None |
| PNP was registered | 5.0 (3 people) | 5.0 (3 people) | 5.0 (3 people) |
| Norm (recovered) | | | 10.0 (6 people) |

Therefore, of the 95% patients that suffered from chronic alcoholism and complications of PNP, after treatment with Ropren 10% had no signs of PNP, i.e., they had recovered. No one had recovered from control group by the end of the treatment. Most of the patients from experimental group had treatment effects by the 15$^{th}$ day. From the Table 6, efficacy of the treatment with the use of Ropren was more evident in patients who suffered from the acute form of PNP, which is comparatively difficult to treat successfully in cases of PNP.

When comparing the two methods of treatment, it was identified that the method for treatment of chronic alcoholism using Ropren was more effective. Recovery from depression and polyneuropathic disorders during chronic alcoholism occurred, on average, two times earlier than with the use of basic therapy. The therapeutic efficacy of basic treatment decreases in patients with a longer duration of disease, whereas using Ropren it increases (Table 7).

Comparative evaluation of therapy activity in control and experimental groups according to hospital anxiety and depression scale (HADS) depending on duration of disease (in points)

TABLE 7

| Mean parameters in control and experimental groups | Duration of disorder up to 5 years | Duration of disorder from 6-10 years | Duration of disorder exceeding 10 years |
|---|---|---|---|
| Mean parameters of control group before treatment | 20.45 ± 4.68 | 21.00 ± 4.45 | 19.50 ± 4.51 |
| Mean parameters of control group after treatment | 5.20 ± 1.81 | 6.00 ± 2.92 | 8.50 ± 1.64 |
| Mean parameters of experimental group before treatment with Ropren | 23.11 ± 2.11 | 24.48 ± 3.53 | 23.29 ± 3.02 |
| Mean parameters of experimental group after treatment with Ropren | 4.74 ± 2.58 | 4.63 ± 2.69 | 3.50 ± 1.29 |

In cases where patients had drug addiction in combination with alcoholism and were treated with Ropren, the regression of neurological symptoms (PNP) was noticed by 15$^{th}$ day of treatment (as assessed by Young's scale). With respect to psychosomatic state, recovery from abstinence syndrome was registered for most of these patients after 3-4 days of treatment, and in others after 16-17 days.

Effect of Ropren on course of chronic alcoholism in combination with intake of narcotic substances is shown in Table 8.

TABLE 8

| | Before treatment | | | After treatment with Ropren | | | | | | |
|---|---|---|---|---|---|---|---|---|---|---|
| | | | | | | Points by Young's scale | | | | |
| No. of patient card | Points by questionnaire | Points by HADS scale | Points by Young's scale | Points by questionnaire | Points by HADS scale | After 15 days | After 30 days | Age | Duration of disease | Disease, drug |
| 1 | 31 | 23 | 4 | 4 | 8 | 4 | 2 | 26 | 3 years | Heroin, hepatitis C |
| 3 | 45 | 25 | 6 | 1 | 7 | 4 | 4 | 24 | 2 years | Heroin, hepatitis C |
| 4 | 51 | 22 | 8 | 4 | 5 | 4 | 0 | 35 | 12 years | Heroin, hepatitis C |
| 5 | 51 | 22 | 3 | 6 | 9 | 0 | 0 | 23 | 3 years | Heroin, hepatitis C |
| 19 | 47 | 22 | 8 | 2 | 4 | 8 | 6 | 33 | 5 years | Heroin, hepatitis C |
| 51 | 49 | 25 | 0 | 0 | 3 | 0 | 0 | 35 | 3 | Heroin, hepatitis C, AID |
| 53 | 46 | 22 | 0 | 1 | 3 | 0 | 0 | 17(f) | 4 | Heroin, hepatitis C, AID |

Patients with problems of drug addiction in combination with alcoholism had marked positive changes in the form of an increase in amplitude and alpha-rhythm indices, which was clear from visual EEG and data obtained from spectral analysis. The functional state of the CNS normalises.

Clinical characteristics of patients before and after treatment in control and experimental (using Ropren) groups are shown in Table 9.

approximately by 1.5 times. Treatment with Ropren increases background mood, and a complete reduction of all anxiety-depressive symptoms in patients occurs much faster. The level of orientation, concentration and capacity to work improves. The psycho stimulative and antiasthenic affect of the treatment is more pronounced in the experimental group. Symptoms of anxiety, irritation, suspiciousness and tearfulness were alleviated faster. Abstinence syndrome was also

TABLE 9

| Parameters | Control group, n = 30 people | | | Experimental group, n = 60 people | | |
|---|---|---|---|---|---|---|
| Age of patients | 62.83 ± 13.89 | | | 56 ± 13.0 | | |
| Men:Women | 27:3 (9:1) | | | 47:13 (3.6:1) | | |
| Duration of disease: | | | | | | |
| up to 5 years | 36.7% (11 people) | | | 31.7% (19 people) | | |
| 6-10 years | 43.3% (13 people) | | | 45% (27 people) | | |
| exceeding 10 years | 20% (6 people) | | | 23.3% (14 people) | | |
| Improvement in psychosomatic state according to hospital anxiety and depression scale (HADS) (Zigmond A. S. and Snaith R. P., 1983) | | | | | | |
| | Before treatment | After treatment | | Before treatment | After treatment | |
| Depression parameters: according to HADS | | | | | | |
| marked depression | 100.0% | 0% | | 100.0% | 0% | |
| improvement in depression state | | 48.3% | | | 78.3% | |
| Depression remains | | 55.2% | | | 21.7% | |
| Improvement of polyneuropathy symptoms according to Young's scale (Neuropathy Disability Score or neuropathy dysfunctional scaling) (Young M. J., 1993, Dyck P. J., 1992) | | | | | | |
| | | Day 15 | Day 30 | | Day 15 | Day 30 |
| according to Young's scale: | | | | | | |
| Moderate form | 13.8% | 17.3% | 34.5% | 23.3% | 58.4% | 76.6 |
| Marked form | 44.8% | 48.3% | 48.3% | 45.0% | 33.3% | 8.4 |
| Severe form | 27.6% | 20.7% | 3.4% | 26.7% | 3.3% | 0.0 |
| PNP was not registered | 13.8% | 13.8% | 13.8% | 5.0% | 5.0% | 15.0 |
| Improvement in neurological state (focal cerebral symptoms) | | | | | | |
| Significant improvement | 10% (3 people) | | | 49.2% (29 people) | | |
| Improvement | 26.7% (8 people) | | | 32.2 (19 people) | | |
| Some improvement | 43.3% (13 people) | | | 15.2% (9 people) | | |
| Without any effect | 13.3% (4 people) | | | 1.7% (1 person) | | |
| Impairment | 6.7% (2 people) | | | 1.7% (1 person) | | |
| Improvement in functional state of CNS according to EEG data | | | | | | |
| Negative changes | 23.5 | | | 2% | | |
| Some changes | 35% | | | 14% | | |
| Ambiguous changes | 18% | | | 18% | | |
| Total | 76.5% | | | 34% | | |
| Some positive changes | 23.5% | | | 24% | | |
| Positive changes | 0.0% | | | 11% | | |
| Marked positive changes | 0.0% | | | 31% | | |
| Total | 23.5% | | | 66% | | |

The efficacy of treatment by both methods of therapy is presented in the summary Table 9. In cases where patients were treated with basic therapy, improvement of psychosomatic state was registered in 55.2% of patients, whereas in the same timeframe, in cases where Ropren was administered, an improvement was found in 80% of patients. In 44.8% of patients in the control group and 20% of patients in the experimental group a depressive state remained after treatment. The data revealed that treatment with Ropren produced faster and significant reduction in depression, alleviated faster in the experimental group, on average by 3-10 days, whereas in the control group this took 14-21 days.

Neurological state measured by cerebral and focal symptoms improved in 10% of patients in the control group, while in the experimental group 49.2% improved by the end of the treatment. Total percentage of "improvement" and "significant improvement" in neurological state of patients for cerebral and focal symptoms in experimental group using Ropren was 81.4%, and in control group 361%. However, it is reasonable to note, that patients in experimental group were initially observed to have more severe psychosomatic and neurological symptoms: a high percentage (24%) of patients used surrogate alcohol, and patients had toxicomania and poisoning, a large number of patients with suicidal tendencies, Karsakov's syndrome and drug addiction—all of which aggravated the course of the main disease.

In 10% out of 95% of patients, who suffered from PNP, the signs of disease had completely disappeared indicating recovery, however in the rest of patients (85%) regression of symptoms of polyneurotic disorders and transformation of patients from severe to marked or moderate stage of disorder was noted, according to Young's scale. Significant improvement in PNP changes occurred by $15^{th}$ day of treatment in patients of experimental group, 58.4% had moderate form of PNP, 33.3%—marked and 3.3%—severe.

According to EEG, expressed efficacy of treatment with the use of Ropren was found. Improvement occurred in 66.0% of patients, marked positive changes in 31.0%, no significant change in 14.0%, and negative change in 2% of patients out the 60 examined. Some patients, after treatment with Ropren, had EEG results within norms. In the control group, an effect received from basic therapy was noted only in 23.5% of patients, which was evident as some positive changes (marked positive changes were not identified), no significant change in 35%, negative change in 35% out of 30 examined patients.

From Table 9, the psychosomatic state after treatment of chronic alcoholism using a generally-accepted basic therapy (control group) decreased by 3.3 times as assessed by the HADS scale. In other words, depression remained.

After treatment with Ropren, the psychosomatic state in patients with chronic alcoholism improved by 5.4 times to normal levels according to the hospital anxiety and depression scale. Based on the obtained data, it can be concluded, that use of Ropren in patients with chronic alcoholism by the suggested methodology provides normalization of the psychosomatic state and recovery from depressive state.

Instances of Expressed Activity of Ropren:

Patient, card No. 1, 35 y.o., duration of the disease—12 years. Drugs of the opium group have been used for more than 17 years, and methadone (i/v)—for more than the last 7 years. Diagnosis: chronic alcoholism, drug addiction (heroin). Main syndrome: abstinence+depressive syndrome. Ropren was prescribed 3 times daily before having food for a period of 1 month on a background of basic therapy. Recovery from abstinence syndrome was registered on the $3^{rd}$ day. According to data from the neurologist, complete regression of focal symptoms and polyneurotic disorders occurs by $30^{th}$ day. Almost all biochemical parameters of blood normalised on 15th day.

Patient, card No. 2, 24 y.o. Drugs of opium group (ephedrine, heroin) have been used from 19 years of age. Patient started to heavily consume alcohol after stopping taking drugs. Ropren was prescribed 3 times daily before having food for a period of 1 month on background of basic therapy. Recovery of abstinence syndrome was registered on $3^{rd}$ day. Positive changes in the neurological state were registered by $15^{th}$ day of treatment: nystagmus disappeared, coordination disorders decreased, tremor of hands had gone, focal neurological symptoms had almost completely regressed by the $30^{th}$ day of treatment, light polyneurological loss of reflexes (from 6 to 4 points) occurred, which testifies a significant improvement of state. The patient came to the doctor asking for more information about the substance, because it was first time that the patient had not wanted to drink alcohol or take drugs for a period of 3 weeks.

Patient, No. 44, 39 y.o. Duration of the disease—10 years. Diagnosis—alcohol abstinence syndrome (AAS), level 2 chronic alcoholism and toxic polyneuropathy. Complete recovery from AAS was registered on $6^{th}$ day, and improvement of symptoms of mental state according to "list of symptoms" and HADS scale on the $15^{th}$ day and absence of depression on the $30^{th}$ day. Significant regression of neurological symptoms was noted on $16^{th}$ day: signs of hallucination disappeared, regression of focal cerebral symptoms, Achilles reflexes, significant regression of PNP (from 10 to 4 points according to Young's scale, in other words improvement from a severe form of PNP to a moderate form) were also registered. According to EEG data, significant amplification of alpha-rhythm and reduction in rhythmic photostimulation occurred after the treatment. EEG data displayed positive changes.

Patient, card No. 4, age 35 y.o., duration of the disease—3 years. Diagnosis: chronic alcoholism of the 2nd level, suicide, drug addiction (heroin), chronic viral hepatitis C, HIV-infection. Biochemical analysis of blood improved on the $15^{th}$ day during the course of treatment with Ropren and normalized on the $30^{th}$ day, and diastase of urine reduced to normal levels—195.5 on $15^{th}$ day of the treatment. Parameters of blood normalized (hemoglobin increased on $15^{th}$ day from 126 to 140 g/l, leukocyte count increased from 4.2 to $6.8$-$10^9$/n, lymphocytes—from 35-40% to 28% (normal levels)). Complete elimination of signs of depression was registered on $30^{th}$ day according to HADS scale and the "list of symptoms". From a neurological perspective, toxic encephalopathy with epileptic syndrome (no signs of PNP) was diagnosed. Significant improvement and complete regress of focal symptoms occurred on the $15^{th}$ day. EEG, before treatment with Ropren, revealed average diffusive changes of bioelectric activity (BEA) in cortices of the large hemispheres with light epileptiform manifestations (in the form of diffusive sharp waves and reduced epicomplexes). After treatment, an increase in the intensity of alpha-activity was revealed by EEG. Marked positive changes were registered by EEG.

The obtained data enables us to conclude that Ropren administration in patients with chronic alcoholism provides normalization of psychosomatic states and recovery from depressive states by using the presented methodology, as well as, from neurological disorders related to consumption of alcohol and/or drugs. Cases of abstaining from consumption of ethyl alcohol by patients were identified for a period of examination and after for more than a month.

As a result of treatment, by $15^{th}$ day biochemical parameters had already indicated a normalization of all parameters in the experimental group: normalization of levels of AP, ALT, AST, MAO, bilirubin, urea, creatinine, amylase and sugar in the blood. This improvement is less marked in the control group of patients.

In case where the duration of the disease was for more than 10 years, the efficacy of the basic therapy (control group) decreases; it is more effective for treatment of disease with duration of less than 5 years. However, the greatest efficacy of treatment with Ropren was registered during disease with duration exceeding 10 years. This testifies to the fundamentals of the metabolic effect of the substance.

There were improvements in mental, neurological and metabolic states during treatment of patients from alcohol and drug addiction with Ropren. Data obtained from EEG revealed positive changes, which are characterised in normalization of CNS, recovery of balances of stimulation and inhibition, spectrum of these changes gains proper organized modulating character and getting closer to the norms.

Therefore, the use of Ropren seems promising for treatment of this group of patients. In addition, there is a possibility for the prospective use of the substance for treatment of patients with drug addiction.

INDUSTRIAL APPLICABILITY

From the above results of the study of the therapeutic substance based on compound of formula (1) conducted in the clinic, one is able to conclude the efficacy of the treatment on addiction to ethyl alcohol and/or drugs, on recovery from abstinence syndrome, and on improvement of psychosomatic state in patients, as well as on significant improvement of neurological disorders and/or complete regression of polyneuropathy.

The use of plant origin substance Ropren in the treatment of the given pathologies is the most favourable because of its low toxicity (taking into account liver and kidney damage in practically all patients with the given nosological form), the possibility of prolonged use and the reduction of side effects of psychotropic substances.

It is reasonable to note that Ropren is well tolerated by patients and side effects, allergic reactions and impairments were not registered in any patient in the experimental group for whole period of treatment. Ropren is not an expensive substance and is obtained by known extraction methods from coniferous verdure.

What is claimed is:

1. A method of treating addiction to ethanol and/or drugs, comprising administering to a patient in need thereof polyprenols of formula (1):

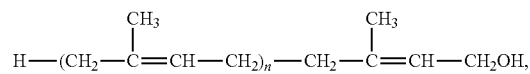

where n=8-20,
wherein said polyprenols of formula (1) are administered in an amount of from 1-150 mg per dose.

2. The method of claim 1 wherein said polyprenols of formula (1) are administered in the form of a solution, suspension, capsule, or tablet, or in liposomal form.

* * * * *